United States Patent [19]

Toda et al.

[11] Patent Number: 4,708,126
[45] Date of Patent: Nov. 24, 1987

[54] ENDOSCOPIC APPARATUS WITH CONNECTING MEANS

[75] Inventors: Masato Toda; Hisao Yabe, both of Tokyo, Japan

[73] Assignee: Olympus Optical Co., Ltd., Tokyo, Japan

[21] Appl. No.: 884,757

[22] Filed: Jul. 11, 1986

[30] Foreign Application Priority Data

Aug. 9, 1985 [JP] Japan ............................. 60-175502

[51] Int. Cl.$^4$ .............................................. A61B 1/06
[52] U.S. Cl. ......................................................... 128/6
[58] Field of Search ......................................... 128/4, 6

[56] References Cited

U.S. PATENT DOCUMENTS

| | | | |
|---|---|---|---|
| 4,253,448 | 3/1981 | Terada ................... | 128/6 X |
| 4,261,345 | 4/1981 | Yamaguchi ............. | 128/6 |
| 4,402,313 | 9/1983 | Yabe ....................... | 128/6 |
| 4,414,608 | 11/1983 | Furihata ................. | 128/6 X |
| 4,534,339 | 8/1985 | Collins et al. ........... | 128/6 |
| 4,539,586 | 9/1985 | Danna et al. ............ | 128/6 X |
| 4,576,144 | 3/1986 | Ishii ......................... | 128/4 |
| 4,601,284 | 7/1986 | Arakawa et al. ........ | 128/6 |

FOREIGN PATENT DOCUMENTS

| | | |
|---|---|---|
| 2152452 | 4/1973 | Fed. Rep. of Germany . |
| 2503219 | 9/1975 | Fed. Rep. of Germany . |
| 2743626 | 4/1978 | Fed. Rep. of Germany . |
| 1953440 | 2/1980 | Fed. Rep. of Germany . |
| 3234738 | 3/1984 | Fed. Rep. of Germany . |
| 57-69837 | 4/1982 | Japan . |

*Primary Examiner*—William H. Grieb
*Attorney, Agent, or Firm*—Frishauf, Holtz, Goodman & Woodward

[57] ABSTRACT

An endoscopic apparatus includes an endoscope body and a drive unit for driving the endoscope body. The endoscope body has a connector which is connected to a socket of the drive unit. The socket is provided with an electrical socket unit, an optical socket unit and a fluid socket unit which have central axes parallel to one another, respectively. The electrical socket unit is supported by support members to be movable in a direction perpendicular to the central axis of the unit. The connector has an electrical connector unit, an optical connector unit and a fluid connector unit which are adapted to be connected to the corresponding socket units. When the connector is connected to the socket, the electrical socket unit is guided by a guide mechanism to a position wherein it is located coaxial with the electrical connector unit.

11 Claims, 12 Drawing Figures

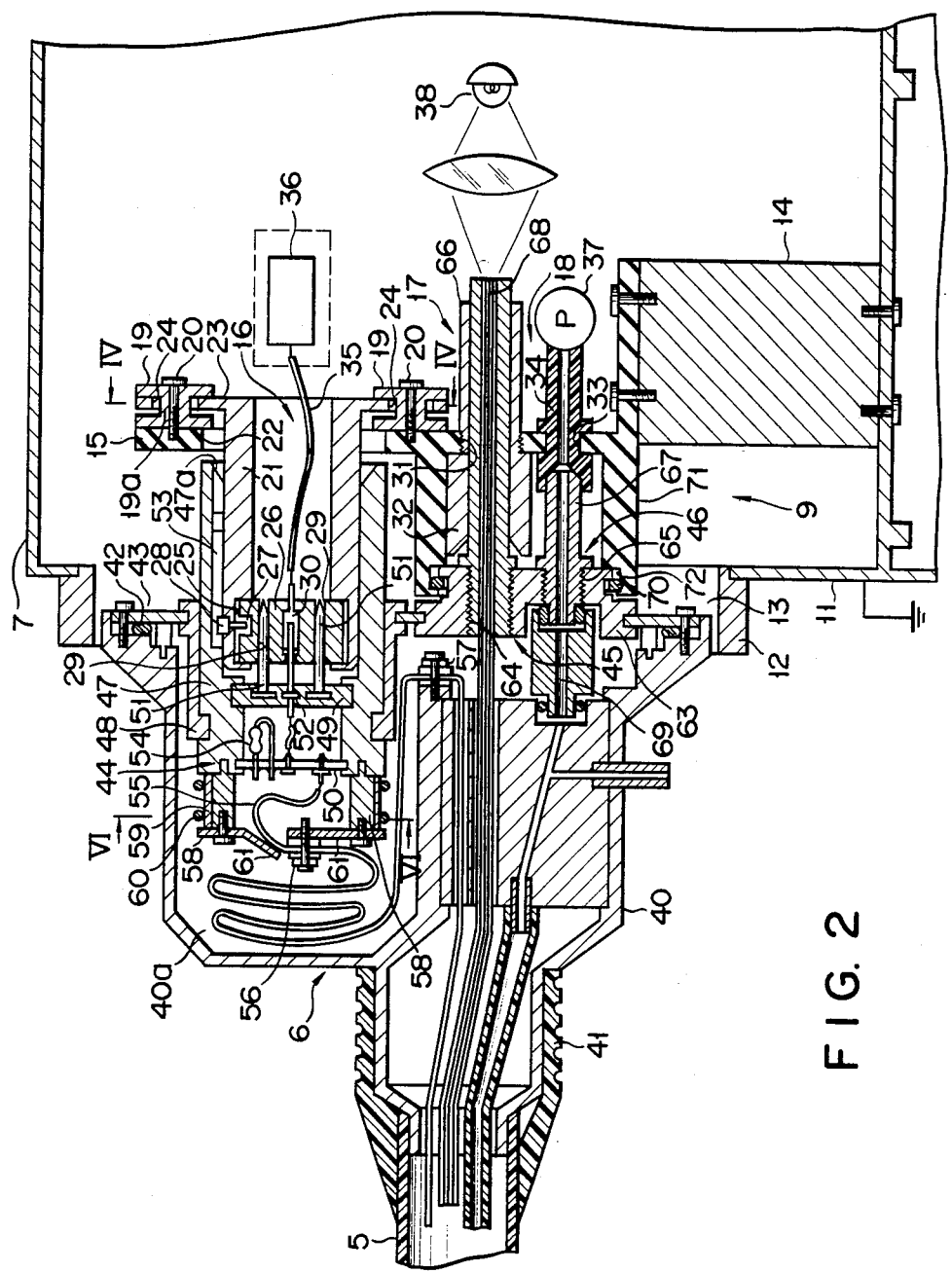
F I G. 2

ENDOSCOPIC APPARATUS WITH CONNECTING MEANS

BACKGROUND OF THE INVENTION

The present invention relates to an endoscopic apparatus having an endoscope body and a drive unit which includes a video processor, light source, etc.

An endoscope may be used for the observation, treatment, or photographing of the inside of the body cavity. In doing this, the body of the endoscope is connected to a drive unit by means of a universal cord, so that the endoscope body is supplied with illumination light, electrical signals, and fluid from the drive unit. The endoscope body is connected to the drive unit by fitting a connector at the distal end of the cord into a socket of the drive unit. The connector and socket are provided with a plurality of connector units and socket units, respectively, for the light, signals, and fluid.

The connector units and socket units can be connected simultaneously by a single connecting operation. Also, electrical contacts can be securely insulated from peripheral metallic parts surrounding them, thus facilitating the prevention of electrical noise at the electrical connecting section. When connecting the connector and socket, each including a plurality of units, however, the individual units of the connector must be accurately aligned with those of the socket. Therefore, the connector and socket must be manufactured with high dimensional accuracy, thereby increasing manufacturing cost.

The maximum allowable connection/disconnection frequency of conventional electrical connectors is relatively low. According to the MIL standards, for example, it is restricted to 500 cycles or thereabout. On the other hand, the endoscope must be washed and cleaned at the end of every operation for observation or treatment, requiring very frequent connection/disconnection between the connector of the endoscope body and the socket of the drive unit. Usually, the frequency of connection/disconnection is 15 cycles a day, on average. If there are five working days per week, therefore, the frequency exceeds 3,500 cycles a year. Accordingly, the connector and socket must be not only easy to handle but also highly durable.

If both electrical and optical connecting sections are made rigid enough to fulfill the aforesaid requirement, the individual components must be manufactured with extremely high accuracy. In the optical connecting section, the quantity of light transmitted to a light guide can be reduced drastically by a slight dislocation between a light source and the incidence end of the light guide. Thus, the positional accuracy must be limited to ±0.5 mm in the axial direction and ±0.15 mm in the radial direction. In the electrical connecting section, if the respective axes of the contacts are subject to a deviation of about 0.2 mm when the connection and disconnection are repeated, the contacts will be quickly worn away. Consequently, the electrical contact resistance may be increased or contact failure may take place.

According to an endoscopic apparatus disclosed in Japanese Patent Disclosure No. 69837/82, a universal cord of an endoscope body includes two branch cords diverging in the middle from each other, and electrical and optical connector means are attached individually to the distal ends of the branch cords. In this case, the dimensional accuracy of the connector means does not matter. However, these connector means must be connected to or disconnected one by one from socket means of a drive unit, thus lowering the operating efficiency. While one connector means is being handled, moreover, the other may possibly swing, touching and damaging a panel of the drive unit.

SUMMARY OF THE INVENTION

The present invention has been contrived in consideration of these circumstances, and is intended to provide an endoscopic apparatus in which an endoscope body and a drive unit can be connected and disconnected easily and securely without requiring high dimensional accuracy at the time of manufacture.

In order to achieve the above object, according to an endoscopic apparatus of the invention, a connector of an endoscope body includes first and second connector units, and a socket of a drive unit to be connected witt the connector includes first and second socket units to which the first and second connector units are connected, respectively. At least one of the connector or socket units is movably supported by support means. The endoscopic apparatus is further provided with guide means for guiding that unit movably supported by the support means to a position where the unit can be connected to its corresponding unit when the connector is connected to the socket.

BRIEF DESCRIPTION OF THE DRAWINGS

FIGS. 1 to 8 show an endoscopic apparatus according to a first embodiment of the present invention, in which FIG. 1 is a perspective view of the apparatus, FIG. 2 is a sectional view showing a connecting section in a state in which a connector of an endoscope body is connected to a socket of a drive unit, FIG. 3 is a sectional view of the connecting section in a state in which the connector is removed from the socket, FIG. 4 is a sectional view taken along line IV—IV of FIG. 2, FIG. 5 is a schematic view showing part of a guide mechanism, FIG. 6 is a sectional view taken along line VI—VI of FIG. 2, and FIGS. 7 and 8 are sectional views individually showing processes of connection between an electrical connector unit and a socket unit;

FIGS. 11 and 12 show an endoscopic apparatus according to a third embodiment of the invention, in which FIG. 11 is a perspective view of the apparatus, and FIG. 12 is a sectional view of a connecting section.

DETAILED DESCRIPTION OF THE PREFERRED EMBODIMENTS

Figure 1:
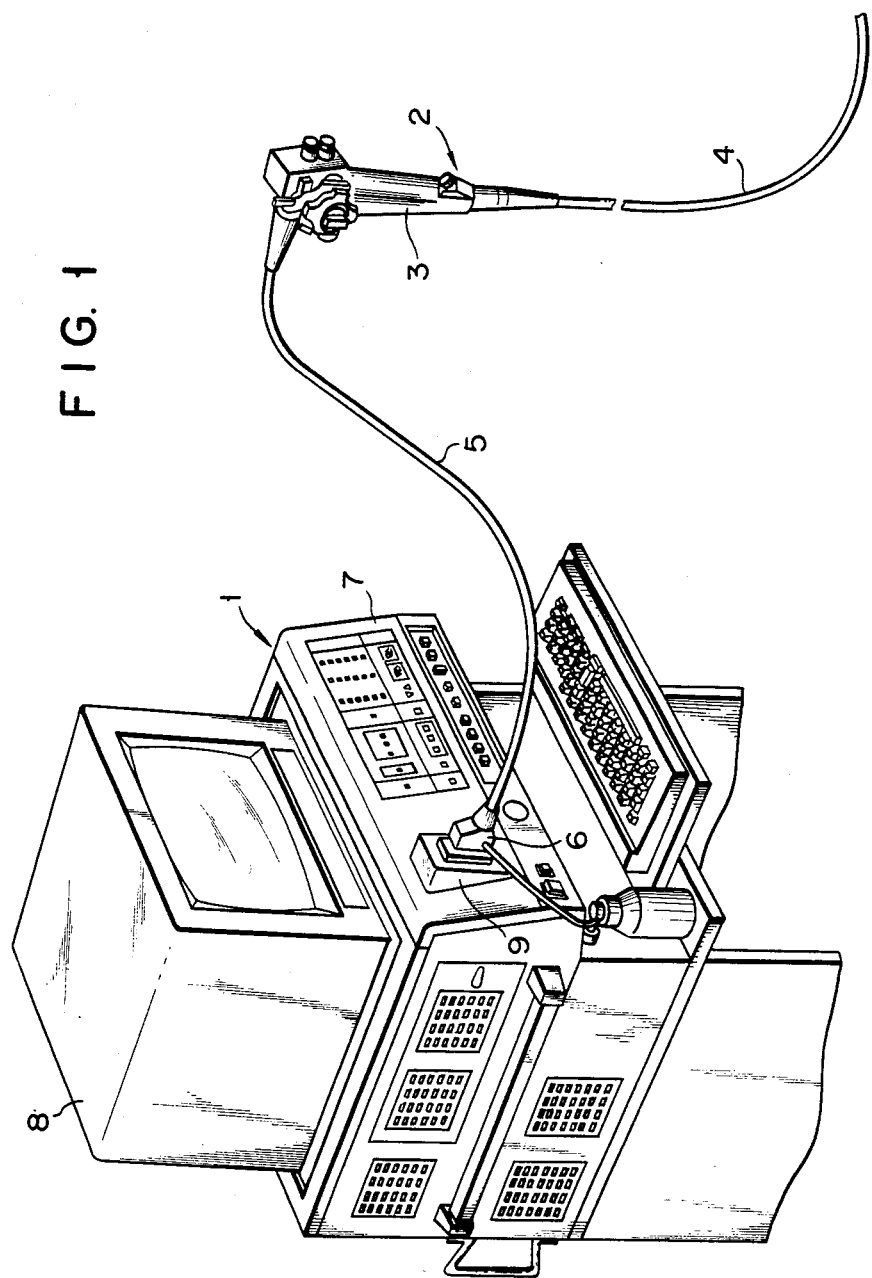

Preferred embodiments of the present invention will now be described in detail with reference to the accompanying drawings:

FIGS. 1 to 8 show an endoscopic apparatus according to a first embodiment of the invention. As shown in FIG. 1, the apparatus comprises endoscope drive unit 1 and endoscope body 2 connected thereto. Body 2 includes operation section 3, insertion section 4 extending therefrom and adapted to be inserted into the body cavity, and universal cord 5 extending from section 3. Connector 6 is attached to the extending end of cord 5. Drive unit 1 includes housing 7 and monitor 8 mounted thereon. Housing 7 contains a video processor, light source unit, etc. Socket 9 is located on the front of housing 7. Optical, electrical, and fluid systems of unit 1 and endoscope body 2 are connected by coupling connector 6, of body 2, to socket 9.

Figure 3:
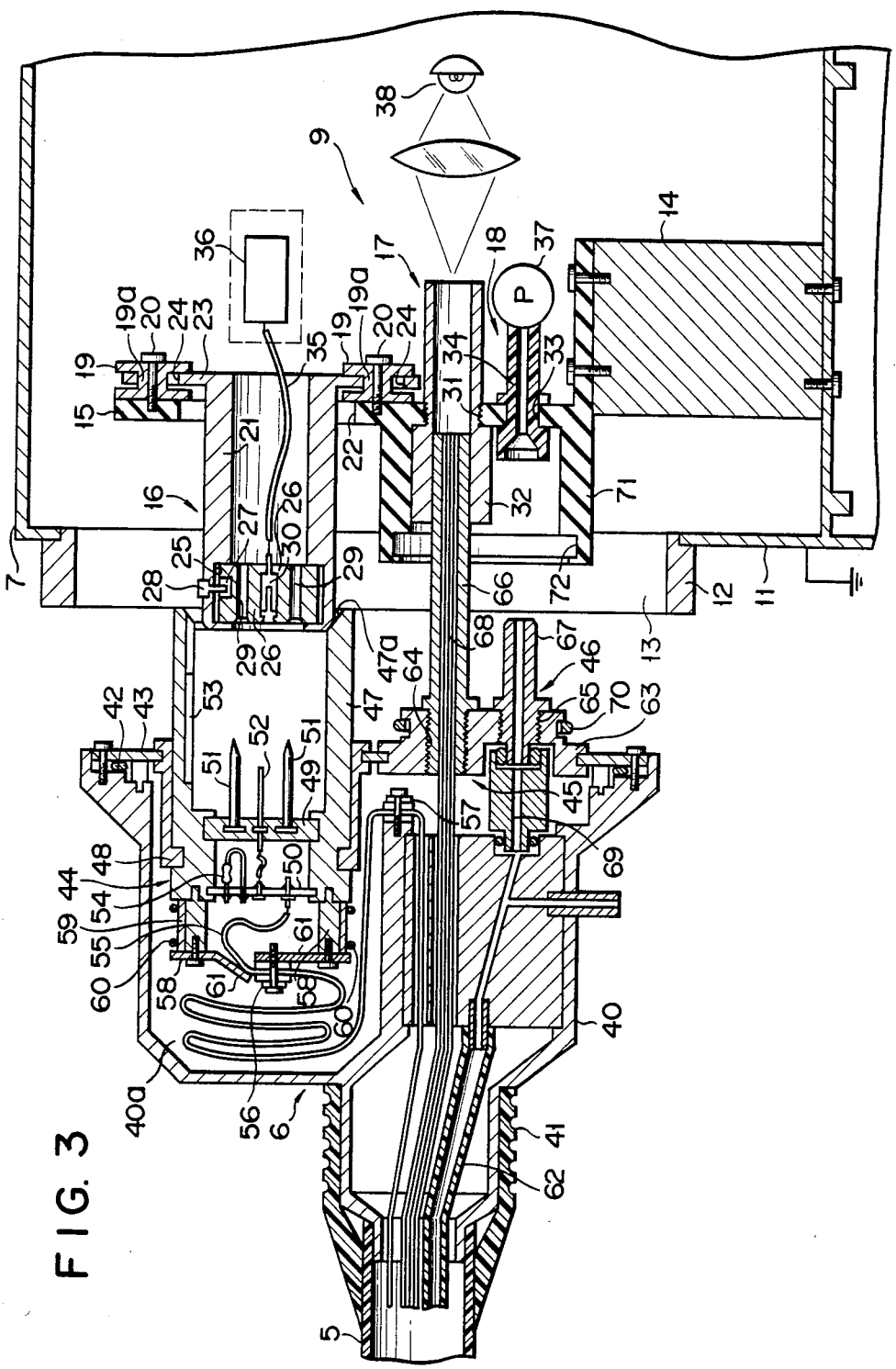

Referring now to FIGS. 2 and 3, connector 6 and socket 9 will be described in detail:

Opening 13 is formed in front panel 11 of drive unit housing 7, and insulating cylinder 12 is fixed to the panel, fringing the opening. Inside housing 7, socket 9 is located near opening 13. The socket includes insulating member 14, fixed to housing 7, and plate-like base 15, which is fixed to member 14 and faces opening 13. Base 15 is fitted with electrical socket unit 16, optical socket unit 17, and fluid socket unit 18, which are spaced vertically.

Figure 4:
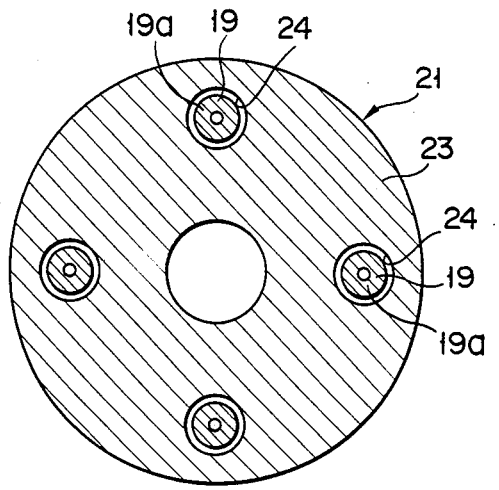
Figure 5:
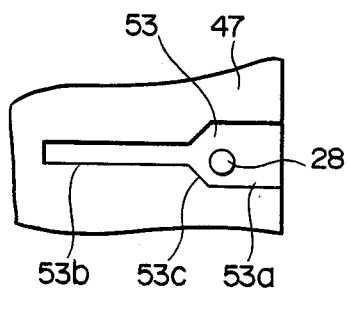
Figure 6:
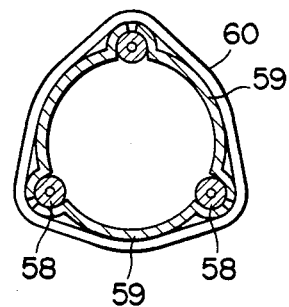

Electrical socket unit 16 includes support cylinder 21 which is passed through a circular opening 22 in the base 15, and projects from the base toward opening 13. The diameter of opening 22 is sufficiently greater than the outside diameter of cylinder 21. As shown in FIGS. 2 and 4, four cylindrical collars 19 are fixed to base 15 by means of fixing screws 20, arranged at regular intervals along the peripheral edge of opening 22. Each collar 19 has small-diameter portion 19a in its central portion, with respect to the axial direction. Cylinder 21 has ring-shaped flange 23 on the outer periphery of its proximal end portion, which engages collars 19. Flange 23 is formed with four fitting holes 24 which are arranged circumferentially at regular intervals. Portions 19a of collars 19 are passed through their corresponding holes 24. The diameter of fitting hole 24 is smaller than that of collar 19 and greater than that of portion 19a. The wall thickness of flange 23 is smaller than the width of small-diameter portion 19a. Thus, cylinder 21 is supported by collars 19 for axial and radial movements relative to base 15.

Annular groove 25 is formed on the inner peripheral surface of the distal end portion of cylinder 21. Cylindrical insulator 26, smaller in diameter than groove 25, is fitted in the groove to be movable in the radial direction of cylinder 21. Regulating hole 27 is formed in the outer peripheral surface of insulator 26, and guide pin 28, penetrating the outer peripheral wall of cylinder 21, engages hole 27. Thus, insulator 26 is restrained from rocking by pin 28. The head of pin 28 projects from the outer peripheral surface of cylinder 21. A plurality of guide holes 29 are bored through insulator 26, extending in the axial direction thereof and of cylinder 21. Also, insulator 26 is provided with an electrical contact 30 which is movable in the axial direction of cylinder 21. Contact 30 is connected to control circuit 36 of the video processor by means of signal wire 35.

Optical socket unit 17 is provided with cylindrical mouthpiece guide 32. Guide 32 is screwed in tapped hole 31 in base 15, and extends parallel to cylinder 21 of electrical socket unit 16, on both sides of the base. Light source unit 38 is located in drive unit housing 7, facing the proximal end of guide 32.

Fluid socket unit 18 is provided with cylindrical mouthpiece holder 34, formed of elastic material, such as rubber. Holder 34 is fitted in mounting hole 33 in base 15, and extends parallel to cylinder 21 of electrical socket unit 16. Pump 37 is connected to the proximal end of holder 34. Socket 9 also includes fitting cylinder 71 which extends parallel to cylinder 21 from base 15 toward opening 13. The respective distal end portions of mouthpiece guide 32 (of optical socket unit 17) and mouthpiece holder 34 (of fluid socket unit 18) are housed in cylinder 71. Annular engaging groove 72 is formed on the inner peripheral surface of the distal end portion of cylinder 7.

Connector 6 will now be described specifically: Connector 6 includes substantially cylindrical case 40, one end portion of which is attached to the distal end of universal cord 5, by means of cylindrical rubber grip 41. The other end opening of case 40 is closed by plate 43 which is attached to the case with the aid of gasket 42. Plate 43 is fitted with electrical connector unit 44, optical connector unit 45, and fluid connector unit 46, corresponding to units 16, 17 and 18, respectively, of socket 9.

Electrical connector unit 44 includes cylindrical support member 47, which is mounted on plate 43 through the medium of insulating member 48, and extends at right angles to plate 43. The inside diameter of member 47 is a little greater than the outside diameter of support cylinder 21, of socket unit 16, so that the former can be fitted on the latter. The proximal end opening of support member 47 is closed by printed board 50, and disk-shaped insulator 49 is fixed in the proximal end portion of the support member, facing the printed board. A plurality of guide pins 51 and connecting terminal 52 extend from insulator 49 toward the distal end of support member 47, in the axial direction of member 47. When member 47 is fitted onto cylinder 21 of socket unit 16, pins 51 are inserted into guide holes 29, of insulator 26, while terminal 52 is connected to electrical contact 30. The inner peripheral surface of the distal end portion of support member 47 is formed with tapered surface 47a spreading out toward the distal end of member 47. Also, the inner peripheral surface of member 47 is formed with guide groove 53, which engages the head of guide pin 28, of socket unit 16. Groove 53 extends from the middle portion of member 47 to its distal end, in its axial direction. As seen from FIG. 5, groove 53 is formed of wide portion 53a on the distal end side of support member 47, narrow portion 53b on the proximal end side of member 47, and slanting portion 53c between portions 53a and 53b. Guide groove 53, tapered surface 47a, and guide pin 28 constitute guide means for guiding cylinder 21 of socket unit 16, at the time of connection.

A plurality of electrical components 54 are fixed on printed board 50, which is electrically connected to connecting terminal 52. One end of electric wire 55 is connected to board 50. Wire 55 extends through universal cord 5, operation section 3, and insertion section 4, to a solid-state image sensor (not shown) which is attached to the distal end of the insertion section. The wire is fixed at two spots or fixing portions 56 and 57, inside case 40. That section of the wire between portions 56 and 57 is contained in inside space 40a of case 40, folded in zigzags. As can be seen from FIGS. 2 and 6, three stays 58 protrude from the proximal end of support member 47, and a plurality of split covers 59 are arranged around the stays. Covers 59 are fixed to stays 58 by means of fixing bands 60. Two shielding plates 61 are attached to the projecting ends of stays 58. Electrical components 54 are protected against noise by plates 61 and covers 59. Fixing portions 56 and 57, for wire 55, are provided on one of plates 61 and the inner wall of case 40, respectively. Each fixing portion is formed of rubber plates and a backup plate.

Cylindrical base 63 is fixed to plate 43, projecting forward therefrom. C-ring 70 is fitted on the outer peripheral surface of the projecting end portion of base 63. When connector 6 is connected to socket 9, base 63 is fitted into fitting cylinder 71 of the socket, and C-ring 70 elastically engages engaging groove 72 of the fitting cylinder. Base 63 is formed with first and second tapped holes 64 and 65. Optical connector unit 45 includes cylindrical light guide mouthpiece 66, which is fixedly screwed into first tapped hole 64, extending from base 63 at right angles thereto. One end portion of light guide 68 formed of an optical fiber, is fixedly inserted in mouthpiece 66. Light guide 68 extends to an illumination window (not shown) at the distal end of insertion section 4, firstly passing through universal cord 5, operating section 3, and then into the insertion section. When base 63 is fitted into fitting cylinder 71, light guide mouthpiece 66 is inserted into mouthpiece guide 32 of socket 9.

Fluid connector unit 46 includes cylindrical fluid mouthpiece 67, which is fixedly screwed into second tapped hole 65, extending from base 63 at right angles thereto. The bore of mouthpiece 67 is connected to fluid tube 62 by means of passage 69, which is formed in case 40. Tube 62 extends to a nozzle (not shown) at the distal end of insertion section 4, firstly passing through universal cord 5, operating section 3, and then into the insertion section. When connector 6 is connected to socket 9, the distal end of mouthpiece 67 is fitted into mouthpiece holder 34 of socket unit 18.

Figure 7:
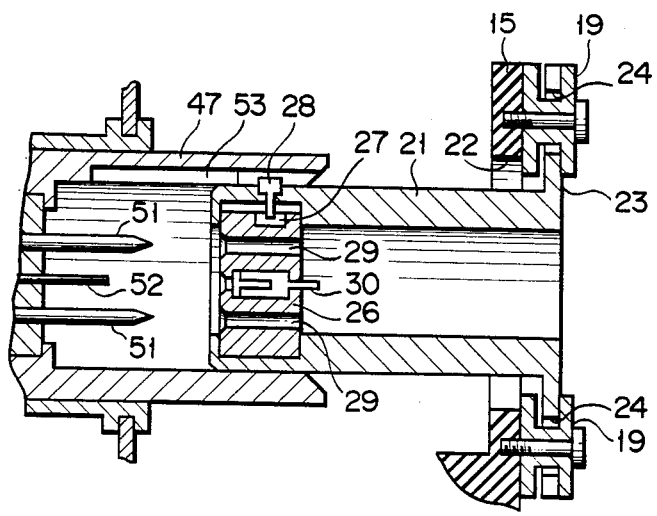

The operation of connector 6 and socket 9, arranged and connected in this manner, will now be described:

When connecting connector 6 to socket 9, the former is inserted into the latter with electrical, optical, and fluid socket units 44, 45 and 46 opposed to socket units 16, 17 and 18, respectively, as shown in FIG. 3. Before connection, support cylinder 21 of socket unit 16 is lowered by its own weight, so that the top of each fitting hole 24 is in contact with small-diameter portion 19a of its corresponding collar 19. First, the distal end of light guide mouthpiece 66 is inserted into mouthpiece guide 32 of socket unit 17 so that tapered face 47a of support member 47 (of connector unit 44), abuts against the distal end of cylinder 21 of socket unit 16. In this state, connector 6 is allowed to rotate freely around light guide mouthpiece 66. Therefore, the position of connector 6 is adjusted so that member 47 faces cylinder 21. If connector 6 is pushed deeper into socket 9, cylinder 21 is guided upward by tapered face 47a of member 47, and finally reaches a position where it is coaxial with member 47. If the connector is further pushed in, guide pin 28 of cylinder 21 enters wide portion 53a of guide groove 53 (of support member 47), as shown in FIG. 7. Since the width of portion 53a is sufficiently greater than the diameter of pin 28, cylinder 21 can move in its circumferential direction when pin 28 is located in portion 53a. Thus, in connecting connector 6, guide pin 28 never fails to enter wide portion 53a of guide groove 53 without regard to the angular position of cylinder 21 relative to collars 19, before the connection.

Figure 8:
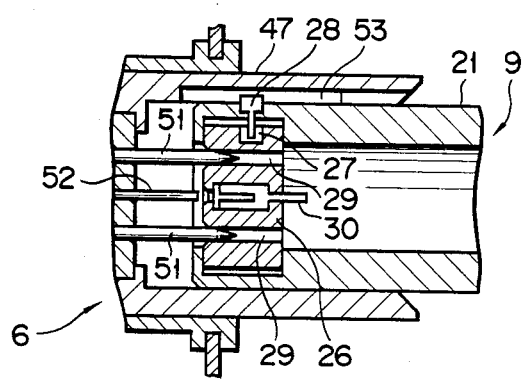

If connector 6 is pushed in deeper, guide pin 28 slides along slanting portion 53c of guide groove 53 into narrow portion 53b, as shown in FIG. 8. While pin 28 is moving past portion 53c, cylinder 21 is rocked, so that its position in its rocking direction, relative to support member 47, is adjusted. Meanwhile, guide pins 51, on the side of member 47, are inserted individually into guide holes 29 of insulator 26, so that the insulator is positioned coaxial with member 47. When connector 6 is fully pushed in, connecting terminal 52 of connector unit 44 is connected to electrical contact 30 of insulator 26, as shown in FIG. 2.

When connector 6 is fully connected to socket 9, the projecting end portion of base 63 of the connector, and C-ring 70 thereon, engage the distal end portion and engaging groove 72, respectively, of fitting cylinder 71, of socket 9. Thereupon, the distal end of light guide mouthpiece 66 projects from the proximal end of mouthpiece guide 32, to face light source unit 38. The projecting end of fluid mouthpiece 67 is fitted into the distal end of mouthpiece holder 34, and fluid passage 69 connects with pump 37. Thus, the electrical, optical, and fluid systems are connected between endoscope body 2 and drive unit 1.

According to the endoscopic apparatus constructed in this manner, electrical socket unit 16 is movable toward and away from socket units 17 and 18. Therefore, if the relative positions of connector units 44, 45, and 46 are not exactly in alignment with those of socket units 16, 17, and 18, the deviation can be corrected by moving unit 16. Thus, connector 6 and socket 9 can be securely connected with ease, even though they are not very high in assembling accuracy. The connector and socket are provided with guide means which guides socket unit 16 to a position where it faces or is coaxial with its corresponding connector unit 44, when the connector is connected to the socket. Accordingly, connector 6 can be connected accurately to socket 9 without regard to the position of socket unit 16 before the connection.

In general, electrical contact 30 and connecting terminal 52 may be formed of tin, gold, or alloy of gold. The contact and terminal can be connected and disconnected 200 times if both of them are formed of tin, and 400 times if formed of gold. If gold, (which is highly tenacious) is used as the material of both contact 30 and terminal 52, the connection and disconnection between these components require a great force. In this embodiment, contact 30 is formed of gilt phosphor bronze, and terminal 52 is of brass plated with an alloy of gold and nickel. Therefore, the necessary force for the connection/disconnection between contact and terminal can be reduced, thus ensuring improved durability of the components.

In connecting or disconnecting connector 6 to or from socket 9, axial reaction is exerted on electrical connector unit 44 and base 63. Since the central axis of rubber grip 41 is located between those of unit 44 and base 63, however, the reaction acts on connector 6 in a well-balanced manner. Thus, connector 6 can be connected and disconnected satisfactorily.

Electric wire 55, which connects circuit board 50 and the solid-state image sensor (not shown), is fixed at two points inside connector case 40. During use of endoscope body 2, or during the process of arranging wire 55 on circuit board 50, therefore, wire 55 can neither be dislocated in universal cord 5 or insertion section 4, nor be broken by high tension. That section of wire 55 between board 50 and fixing portion 57 is so long that the wire can be drawn out to be newly exposed for repair work.

Drive unit housing 7 is formed of metal and is grounded. Insulating member 14 is interposed between housing 7 and base 15, and insulating cylinder 12 is attached to opening 13, of panel 11. Thus, connector 6 and endoscope body 2 are insulated from drive unit 1, while connector case 40 and base 15 are connected electrically.

It is to be understood that the present invention is not limited to the embodiment described above, and that various changes and modifications may be effected therein by one skilled in the art without departing from the scope or spirit of the invention.

Figure 9:
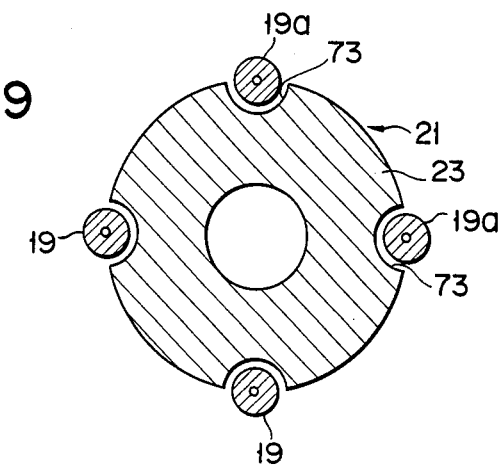
FIG. 9 is a sectional view similar to FIG. 4 showing a modified example of support means.

For example, the means for movably supporting support cylinder 21 of electrical socket unit 16 may alternatively be constructed as shown in FIG. 9. In this case, flange 23 of cylinder 21 has four arcuate notches 73 formed on its outer peripheral edge. Small diameter portions 19a of collars 19 are fitted individually in the notches. With this arrangement, flange 23 can be reduced in outside diameter, so that the whole body of socket 9 can be miniaturized.

Figure 10:
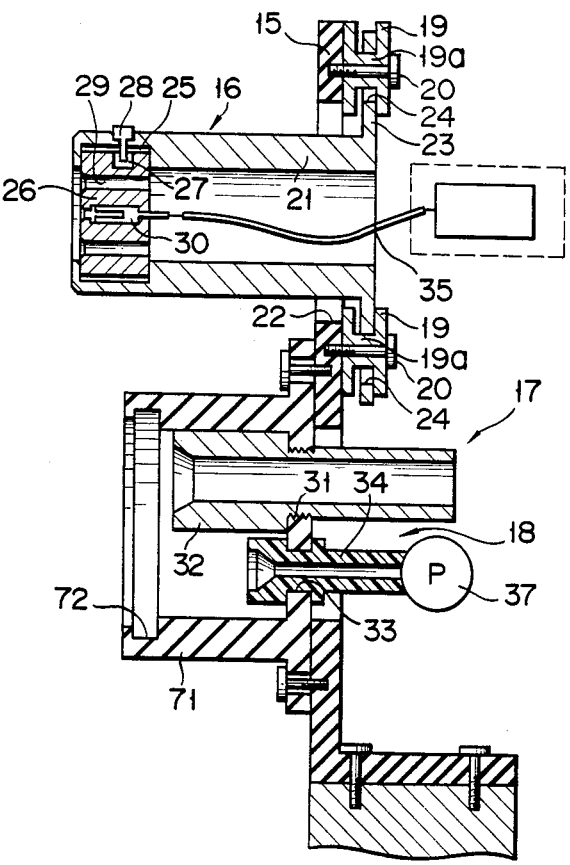
FIG. 10 is a sectional view showing socket units of an endoscopic apparatus according to a second embodiment of the invention.

As shown in FIG. 10, optical socket unit 17 and fluid socket unit 18, as well as electrical socket unit 16, may be arranged for vertical movement. In this case, mouthpiece guide 32 and mouthpiece holder 34 are fixed to fitting cylinder 71, which is movably supported on base 15. With this arrangement, the assembling accuracy of connector 6 and socket 9 is lower.

In the above embodiments, the unit or units on the socket side are movable. Alternatively, the units on the connector side may be arranged for movement.

Figure 11:
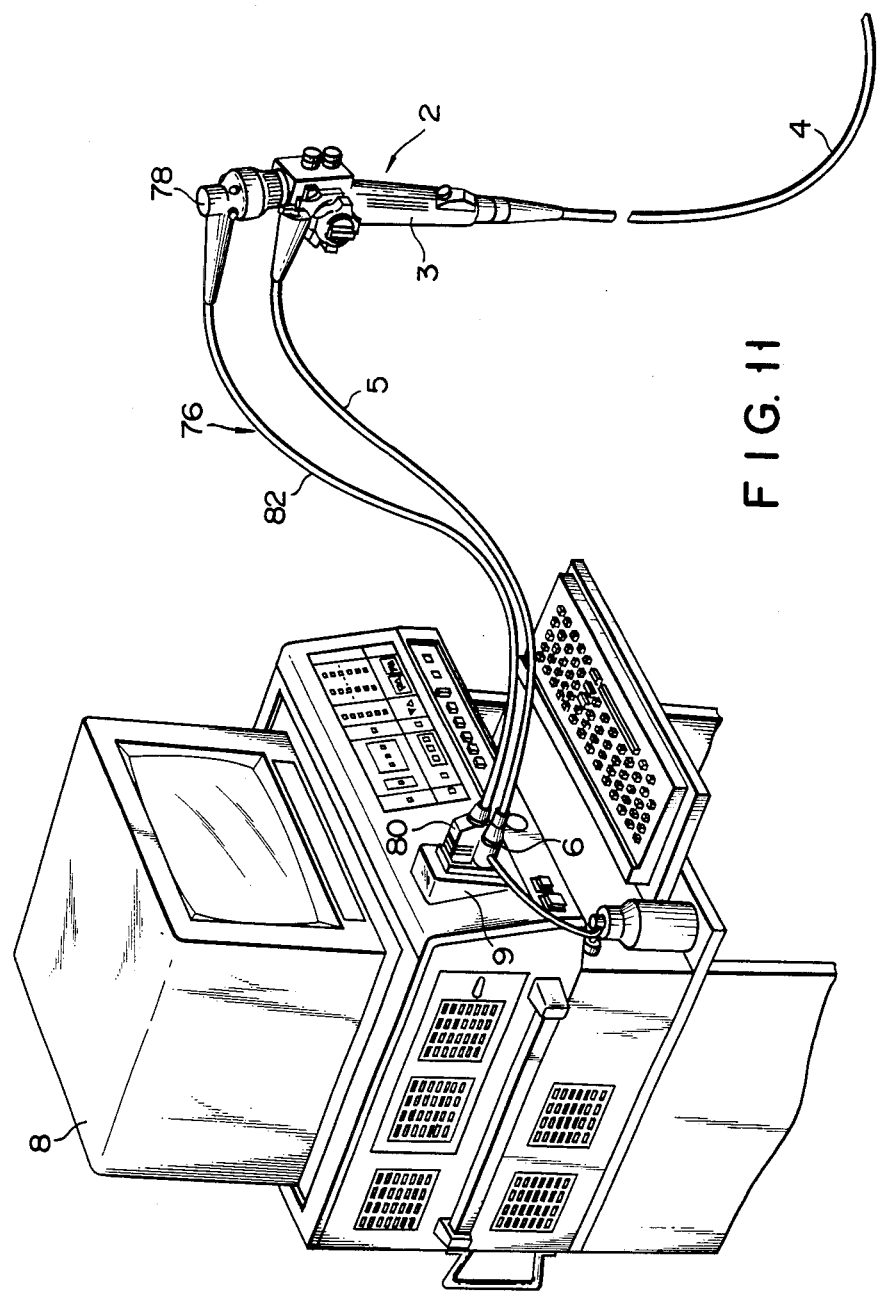
Figure 12:
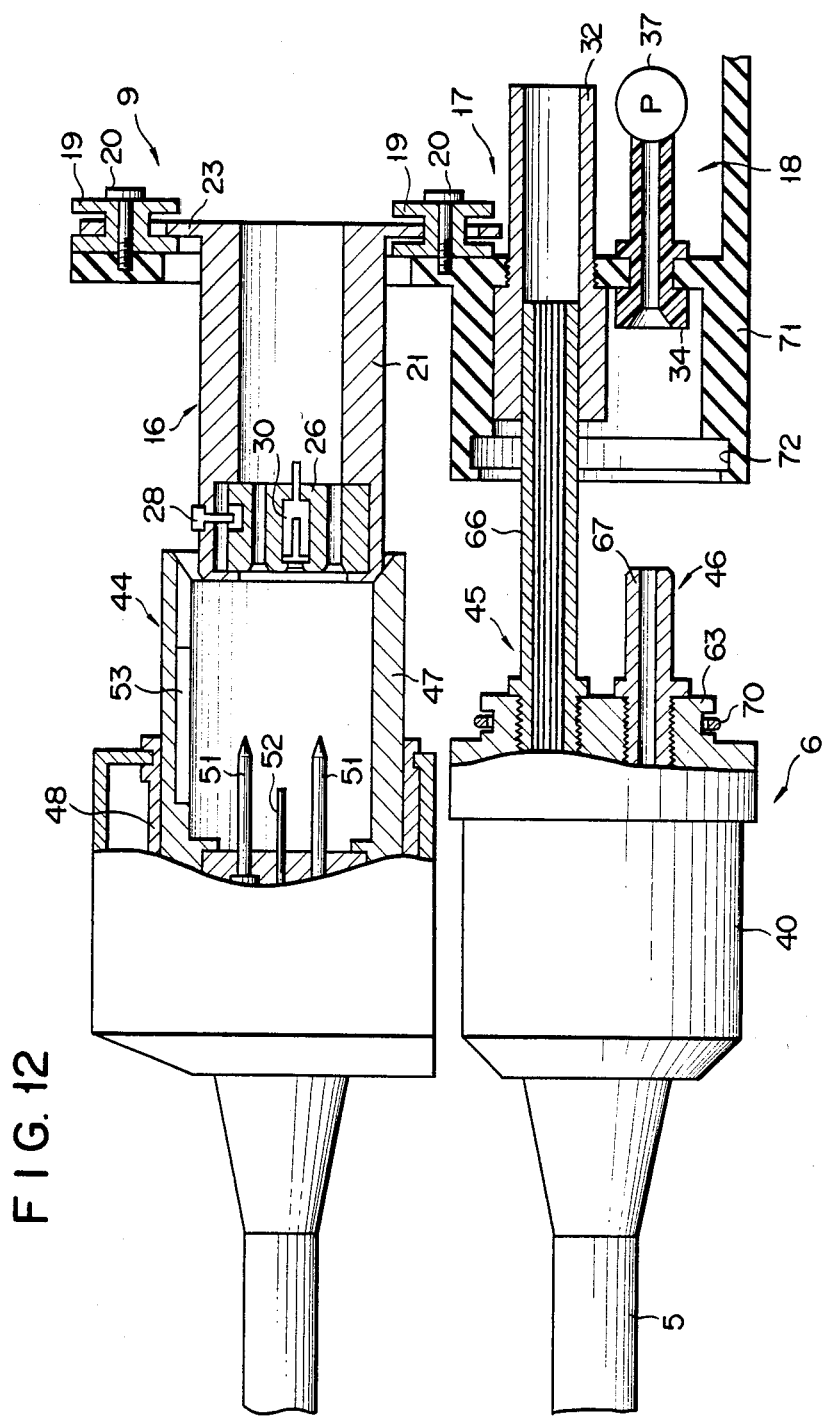

FIGS. 11 and 12 show an alternative embodiment in which endoscope body 2, different in configuration from that of the first embodiment, is connected to drive unit 1. According to this embodiment, body 2 includes no solid-state image sensor, and has a conventional arrangement such that an optical fiber, extending from an eyepiece portion (not shown) at operating section 3, is used for observing an object. Connector 6 of this endoscope body includes only optical and fluid connector units 45 and 46, which are connected to their corresponding socket units 17 and 18 of drive unit 1. When displaying an image, obtained with use of endoscope body 2, on monitor 8 of drive unit 1, body 2 and unit 1 are connected by means of adapter 76. The adapter includes first connector 78 connected to the eyepiece portion of body 2, second connector 80 connected to socket 9 of drive unit 1, and cord 82 connecting the two connectors. A solid-state image sensor is located in first connector 78. It is used to convert the image delivered to the eyepiece portion into an electrical signal and transmit the signal to second connector 80, through cord 82. Connector 80 includes connector unit 44, which is connected to electrical socket unit 16, of socket 9. Unit 44 has the same construction as that of the first embodiment.

What is claimed is:
1. An endoscopic apparatus comprising:
 an endoscope body including an operating section, an insertion section extending from the operating section and adapted to be inserted into the body cavity, a universal cord extending from the operating section, and a connector attached to the extending end of the universal cord, said connector including a first connector unit with a central axis for an optical system, and a second connector unit having a central axis substantially parallel to that of the first connector unit, and spaced at a predetermined distance from the first connector unit;
 a drive unit for driving the endoscope body, said drive unit including a socket detachably connected with the connector, said socket including a first socket unit having a central axis and adapted to be coaxially connected with the first connector unit, and a second socket unit having a central axis substantially parallel to that of the first socket unit and adapted to be coaxially connected with the second connector unit;
 support means for supporting at least one of the connector units or socket units so that the unit can move at right angles to the central axis thereof; and
 guide means for guiding the movably supported unit to a position where the unit is coaxial with its corresponding unit when the connector is connected to the socket.

2. The endoscopic apparatus according to claim 1, wherein said socket includes a base, said second socket unit includes a support cylinder supported on the base for radial movement by the support means and extending from the base, and said second connector unit includes a cylindrical support member having an open free end and adapted to be fitted on the support cylinder.

3. The endoscopic apparatus according to claim 2, wherein said guide means includes a tapered face formed on the inner peripheral edge of the free end portion of the support member and adapted to engage the extending end of the support cylinder, a guide groove formed on the inner peripheral surface of the support member in the axial direction thereof and extending to the free end of the support member, and a guide pin projecting from the outer peripheral surface of the extending end portion of the support cylinder and adapted to engage the guide groove.

4. The endoscopic apparatus according to claim 3, wherein said guide groove includes a wide portion located on the free end side of the support member and having a width sufficiently greater than the diameter of the guide pin, a narrow portion having a width substantially equal to the diameter of the guide pin, and a slanting portion located between the wide and narrow portions.

5. The endoscopic apparatus according to claim 2, wherein said support cylinder includes a ring-shaped flange formed on the outer peripheral surface thereof and a plurality of engaging portions formed on the flange at circumferential intervals, and said support means includes a plurality of engaging members attached to the base and engaging the engaging portions.

6. The endoscopic apparatus according to claim 5, wherein each of said engaging portions includes a through hole bored through the flange, and said engaging members are smaller in diameter than the through holes and are inserted in their corresponding through holes.

7. The endoscopic apparatus according to claim 2, wherein said second connector unit and said second socket unit constitute a connection unit for electrical connection between the endoscope body and the drive unit.

8. The endoscopic apparatus according to claim 7, whereih said second connector unit includes an insulator fixed to the support member, a plurality of guide pins projecting parallel to the central axis of the support member from the insulator, toward the free end of the support member, and a connecting terminal projecting parallel to the central axis of the support member from the insulator, toward the free end of the support member; and said second socket unit includes another insulator supported inside the extending end portion of the support cylinder, so as to be movable in the radial direction of the support cylinder, said second insulator having a plurality of guide holes extending in the axial direction of the support cylinder and adapted individually to receive the guide pins, and an electrical contact connected with the connecting terminal.

9. The endoscopic apparatus according to claim 1, wherein said socket includes a base, said support means includes a fitting cylinder supported on the base, so as to be movable at right angles to the central axis of the first socket unit, said first socket unit includes a cylindrical mouthpiece guide fixed to the fitting cylinder, and said first connector unit includes a cylindrical light guide mouthpiece adapted to be inserted into the mouthpiece guide.

10. The endoscopic apparatus according to claim 9, wherein said connector includes a third connector unit having a central axis parallel to that of the first connector unit, and said socket includes a third socket unit having a central axis parallel to that of the first socket unit and fixed to the fitting cylinder, said third socket unit being adapted to be connected with the third connector unit, said third connector unit and said third socket unit constituting a connection unit for fluid connection between the endoscope body and the drive unit.

11. The endoscopic apparatus according to claim 1, wherein said connector includes a third connector unit having a central axis parallel to that of the first connector unit, and said socket includes a third socket unit having a central axis parallel to that of the first socket unit and adapted to be connected with the third connector unit, said second connector unit and said second socket unit constituting a connection unit for electrical connection between the endoscope body and the drive unit, said third connector unit and said third socket unit constituting a connection unit for fluid connection between the endoscope body and the drive unit.

* * * * *